(12) United States Patent
Suzuki et al.

(10) Patent No.: US 7,947,853 B2
(45) Date of Patent: May 24, 2011

(54) PROCESS FOR PRODUCTION OF NITROGENATED COMPOUND

(75) Inventors: Yuuta Suzuki, Wakayama (JP); Yasuyuki Mimura, Wakayama (JP); Tetsuaki Fukushima, Wakayama (JP)

(73) Assignee: Kao Corporation, Tokyo (JP)

( * ) Notice: Subject to any disclaimer, the term of this patent is extended or adjusted under 35 U.S.C. 154(b) by 9 days.

(21) Appl. No.: 12/518,888

(22) PCT Filed: Nov. 5, 2007

(86) PCT No.: PCT/JP2007/071476
§ 371 (c)(1),
(2), (4) Date: Aug. 6, 2009

(87) PCT Pub. No.: WO2008/072428
PCT Pub. Date: Jun. 19, 2008

(65) Prior Publication Data
US 2010/0029988 A1 Feb. 4, 2010

(30) Foreign Application Priority Data

Dec. 15, 2006 (JP) ................................. 2006-338815

(51) Int. Cl.
*C07C 209/16* (2006.01)
(52) U.S. Cl. ........................................ 564/480; 564/479
(58) Field of Classification Search ........................ None
See application file for complete search history.

(56) References Cited

U.S. PATENT DOCUMENTS

| 5,916,838 | A |   | 6/1999 | Wulff-Doering et al. |        |
|-----------|---|---|--------|----------------------|--------|
| 5,958,825 | A |   | 9/1999 | Wulff-Doering et al. |        |
| 6,057,442 | A | * | 5/2000 | Wulff-Doring et al.  | 544/106 |

FOREIGN PATENT DOCUMENTS

| JP | 07 206788  | 8/1995 |
| JP | 08 243392  | 9/1996 |
| JP | 09 87235   | 3/1997 |
| JP | 10 174874  | 6/1998 |
| JP | 10 174875  | 6/1998 |
| JP | 2001 151734 | 6/2001 |
| JP | 2007 176891 | 7/2007 |
| JP | 2007 197422 | 8/2007 |

OTHER PUBLICATIONS

Database CAPLUS on STN, Acc. No. 1999:321988, Advances of Alcohol Fuels in the World, Proceedings of International Symposium on Alcohol Fuels, 12$^{th}$, Beijing, Sep. 21-24, 1998, 43-48 (abstract).*

* cited by examiner

*Primary Examiner* — Brian J Davis

(74) *Attorney, Agent, or Firm* — Oblon, Spivak, McClelland, Maier & Neustadt, L.L.P.

(57) ABSTRACT

The present invention relates to a process for producing an aliphatic primary amine or an aliphatic secondary amine from an aliphatic alcohol with a high catalytic activity and a high selectivity. In the process for producing an aliphatic amine according to the present invention, a linear, branched, or cyclic aliphatic alcohol having 6 to 22 carbon atoms is contacted with ammonia and hydrogen in the presence of a catalyst formed by supporting a ruthenium component on at least one material selected from the group consisting of (B) a zirconia-containing composite oxide and (C) zirconia surface-treated with a metal by hydrolysis of (A) a ruthenium compound.

19 Claims, No Drawings

PROCESS FOR PRODUCTION OF NITROGENATED COMPOUND

CROSS REFERENCES TO RELATED APPLICATIONS

This application is a 371 of International Patent Application No. PCT/JP2007/071476, filed on Nov. 5, 2007, and claims priority to Japanese Patent Application No. 2006-338815, filed on Dec. 15, 2006.

TECHNICAL FIELD

The present invention relates to a process for producing nitrogen-containing compounds, in particular, aliphatic amines, and more particularly, to a process for producing aliphatic amines using a ruthenium-based catalyst with a high catalytic activity and a high selectivity.

BACKGROUND ART

Aliphatic primary amines and aliphatic secondary amines are important compounds in domestic and industrial application fields and have been used as raw materials for production of surfactants, fiber-treating agents, etc.

The aliphatic primary amines and aliphatic secondary amines have been produced by various processes. As one of the production processes, there is known the method of contacting an aliphatic alcohol with ammonia and hydrogen in the presence of a catalyst. In the catalytic reaction, there has been used a nickel/copper-based catalyst or a noble metal-based catalyst.

As the methods for producing amines from alcohols, etc., using the noble metal-based catalyst, in particular, a ruthenium-based catalyst, there are disclosed, for example, the method using a catalyst formed by supporting about 0.001 to about 25% by weight of ruthenium and about 0.1 to about 6% by weight of cobalt and/or nickel together with about 0 to about 10% by weight of copper and about 0 to about 5% by weight of an accelerator composed of various metals on a porous oxide such as alumina, silica and an aluminosilicate (refer to Patent Document 1), and the method using a catalyst formed by supporting about 0.001 to about 25% by weight of ruthenium and about 6 to about 50% by weight of cobalt and/or nickel together with about 0.1 to about 10% by weight of copper and about 0 to about 5% by weight of an accelerator composed of various metals on a porous oxide such as alumina, silica and an aluminosilicate (refer to Patent Document 2), etc.
Patent Document 1: JP 10-174874A
Patent Document 2: JP 10-174875A

DISCLOSURE OF THE INVENTION

Problem to be Solved by the Invention

However, in these conventional techniques, the catalysts are produced by an impregnating method in which the catalyst produced is dried, calcined at 400° C. for 4 h, and then subjected to hydrogen reduction treatment at 300° C. for 20 h. Further, the conventional catalysts fail to exhibit sufficient reactivity and selectivity.

The present invention provides a process for producing an aliphatic primary amine and/or an aliphatic secondary amine from an aliphatic alcohol with a high catalytic activity and a high selectivity.

Means for Solving Problem

The present invention relates to a process for producing an aliphatic amine, including the step of contacting a linear, branched, or cyclic aliphatic alcohol having 6 to 22 carbon atoms with ammonia and hydrogen in the presence of a catalyst formed by supporting a ruthenium component on at least one material selected from the group consisting of (B) a zirconia-containing composite oxide and (C) zirconia surface-treated with a metal by hydrolysis of (A) a ruthenium compound.

Effect of the Invention

In accordance with the present invention, a aliphatic primary amine and/or an aliphatic secondary amine can be produced from an aliphatic alcohol with a high catalytic activity and a high selectivity.

BEST MODE FOR CARRYING OUT THE INVENTION

In the process for producing an aliphatic amine according to the present invention, as the raw material, a linear, branched, or cyclic (ring-containing) aliphatic alcohol having 6 to 22 carbon atoms is used. From the viewpoints of a good reactivity and a high selectivity, preferred is a linear, branched, or cyclic aliphatic alcohol having 8 to 22 carbon atoms, and more preferred is a linear aliphatic alcohol having 8 to 22 carbon atoms. The aliphatic alcohol used above may be either saturated or unsaturated.

Specific examples of the aliphatic alcohol include hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, 3,7-dimethyloctyl alcohol, 2-propylheptyl alcohol, dodecyl alcohols such as lauryl alcohol, tetradecyl alcohols such as myristyl alcohol, hexadecyl alcohols, oleyl alcohol, octadecyl alcohols such as stearyl alcohol, behenyl alcohol, icosyl alcohols, geraniol, cyclopentyl methanol, cyclopentenyl methanol, cyclohexyl methanol and cyclohexenyl methanol.

In the present invention, the aliphatic amine is produced in the presence of the catalyst formed by supporting a ruthenium component on at least one material selected from the group consisting of (B) a zirconia-containing composite oxide and (C) zirconia surface-treated with a metal by hydrolysis of (A) a ruthenium compound (hereinafter this catalyst is occasionally referred to merely as a "ruthenium-based catalyst").

The zirconia-containing composite oxide (B) means a composite oxide containing zirconia and at least one other metal oxide. From the viewpoints of a good reactivity and a high selectivity to aliphatic primary amines, (B) the zirconia-containing composite oxide preferably contains a zirconium component and at least one metal component selected from the group consisting of molybdenum, calcium, cerium, lanthanum, aluminum, yttrium, silicon, titanium, sulfur and phosphorus. The zirconia-containing composite oxide (B) is more preferably a composite oxide containing zirconia and an oxide of at least one metal selected from the group consisting of calcium, cerium, lanthanum, aluminum, yttrium, silicon, titanium and sulfur, and still more preferably a composite oxide containing zirconia and an oxide of at least one metal selected from the group consisting of cerium, yttrium, silicon, titanium and sulfur.

The content of the other metal oxide used together with zirconia in (B) the zirconia-containing composite oxide is preferably from 0.01 to 25% by mass and more preferably from 0.1 to 15% by mass in terms of the constitutional metal of the other metal oxide on the basis of a total amount of the catalyst from the viewpoints of a good reactivity and a high selectivity to aliphatic primary amines. The content ratio of the other metal oxide to zirconia is preferably from 0.001 to 0.2 and more preferably from 0.01 to 0.1 in terms of a mass ratio of the constitutional metal of the other metal oxide to zirconia (constitutional metal of the other metal oxide/zirconia) from the viewpoints of a good reactivity and a high selectivity to aliphatic primary amines.

The zirconia-containing composite oxide (B) may be produced by an ordinary precipitation method as described, for example, in C. E. Hori, et al., "Appl. Catal.", B16, p. 105 (1998). In the following, a method for producing zirconia-cerium oxide is described as an example of the method for production of (B) the zirconia-containing composite oxide.

A solution prepared by dissolving ammonium cerium nitrate and zirconium nitrate in a medium such as ion-exchanged water is mixed with an alkali to adjust a pH of the solution to preferably from about 7 to about 12 and more preferably from about 9 to about 12 for subjecting these nitrates to hydrolysis, and then the resulting reaction solution is aged to precipitate hydroxides. The alkali used in the above method is not particularly limited, and as the alkali, there may be used carbonates and hydroxides of alkali metals such as sodium and potassium, aqueous ammonia, ammonium hydroxide, etc. The resulting hydroxides are subjected to solid-liquid separation by filtration, etc., and the obtained solid is fully washed with water and then calcined at a temperature of preferably from 400 to 800° C. and more preferably from 500 to 700° C.

The zirconia surface-treated with a metal (C) is obtained by surface-treating the zirconia with metal component. From the viewpoint of a high selectivity to aliphatic primary amines, (C) the zirconia surface-treated with a metal is preferably zirconia surface-treated with at least one metal component selected from the group consisting of molybdenum, calcium, cerium, lanthanum, aluminum, yttrium, silicon, titanium, sulfur and phosphorus, more preferably zirconia surface-treated with at least one metal selected from the group consisting of calcium, cerium, lanthanum, aluminum, yttrium, silicon, titanium and sulfur.

In the surface treatment, zirconia is impregnated with the metal component, or is dispersed in a solution containing a salt of the metal, to support the metal component on zirconia, and then the resulting metal component-supporting zirconia is calcined. More specifically, zirconia is surface-treated with the metal component using nitrates, sulfates, carbonates, hydroxides, oxides, etc., of the metal.

The content of the metal component used in the above surface treatment in the catalyst is preferably from 0.01 to 25% by mass and more preferably from 0.1 to 15% by mass in terms of the metal as the metal component on the basis of a total amount of the catalyst from the viewpoints of a good reactivity and a high selectivity to aliphatic primary amines. The content ratio of the metal component to zirconia (metal as the metal component/zirconia) is preferably from 0.001 to 0.2 and more preferably from 0.01 to 0.1 in terms of a mass ratio therebetween from the viewpoints of a good reactivity and a high selectivity to aliphatic primary amines.

The zirconia surface-treated with a metal (C) may be produced by an ordinary method as described, for example, in J. Yori et al., "Appl. Catal.", A129, p. 83 (1995). In the following, a method for producing zirconia-sulfuric acid as a composite oxide of zirconia and sulfur is described as an example of the method for production of (C) the zirconia surface-treated with a metal.

A solution prepared by dissolving zirconium chloride oxide octahydrate in a medium such as ion-exchanged water is mixed with an alkali to adjust a pH of the solution to preferably from about 7 to about 12 and more preferably from about 9 to about 12 for subjecting the salt to hydrolysis, and then the resulting reaction solution is aged to precipitate a hydroxide. The alkali used in the above method is not particularly limited, and as the alkali, there may be used carbonates and hydroxides of alkali metals such as sodium and potassium, aqueous ammonia, ammonium hydroxide, etc. The resulting hydroxide is subjected to solid-liquid separation by filtration, etc., and the obtained solid is fully washed with water, dried and then dispersed in a 0.5 M sulfuric acid aqueous solution. The resulting dispersion is subjected again to solid-liquid separation by filtration, etc., dried and then calcined at a temperature of preferably from 400 to 800° C. and more preferably from 500 to 700° C.

These zirconia-containing composite oxides (B) and these zirconias surface-treated with a metal (C) may be respectively used singly or in combination of any two or more thereof.

The ruthenium-based catalyst is formed by supporting (A) the ruthenium component preferably together with (D) the Group VIII metal component on (B) the zirconia-containing composite oxide and/or (C) the zirconia surface-treated with a metal. Specific examples of (D) the Group VIII metal component include nickel, cobalt, palladium, rhodium and iridium. Among these metal components, from the viewpoints of a good catalytic activity and a high selectivity, preferred is a nickel component.

The catalyst used in the present invention is obtained by the method of supporting the ruthenium component preferably together with the Group VIII metal component on (B) the zirconia-containing composite oxide and (C) the zirconia surface-treated with a metal by subjecting sources of these components to hydrolysis.

In the following, an example of the method for producing the catalyst is explained.

First, (B) the zirconia-containing composite oxide and/or (C) the zirconia surface-treated with a metal are added to a medium such as ion-exchanged water and suspended therein, and then a solution prepared by dissolving (A) the ruthenium compound, preferably together with a metal compound (I) as a Group VIII metal component source (i.e., as the component (B)) in a medium such as ion-exchanged water, is added to the resulting suspension. The obtained suspension is heated, if necessary while stirring, to control a temperature thereof to preferably from about 20 to about 95° C. and more preferably from 40 to 80° C.

Examples of (A) the ruthenium compound include chlorides, nitrates, formates, ammonium salts, etc., of ruthenium. Among these ruthenium compounds, from the viewpoints of a good reactivity and a high selectivity to aliphatic primary amines, preferred are chlorides of ruthenium. Examples of the metal compound (I) as the Group VIII metal component source (i.e., as the component (B)) include chlorides, nitrates, sulfates, carbonates, formates, ammonium salts, etc., of the Group VIII metal. From the viewpoints of a high selectivity to aliphatic primary amines, preferred are chlorides, nitrates and sulfates of the Group VIII metal.

Next, an alkali is added to the obtained suspension to adjust a pH of the suspension to preferably from 5 to 12 and more preferably from 6 to 11, thereby allowing the respective compounds to be hydrolyzed. Then, the obtained reaction mixture was aged to support the ruthenium component and the secondary metal component on the zirconia-containing composite oxide and/or the zirconia surface-treated with a metal. The alkali used in the above method is not particularly limited.

Examples of the alkali usable in the above method include carbonates and hydroxides of an alkali metal such as sodium and potassium, aqueous ammonia and ammonium hydroxide.

Next, the ruthenium-based catalyst is preferably subjected to reducing treatment from the viewpoints of a good reactivity and a high selectivity to aliphatic primary amines. More specifically, the reducing treatment is carried out at a temperature of preferably from about 20 to about 95° C. and more preferably from 60 to 95° C., by adding a reducing agent such as, for example, formaldehyde, hydrazine and sodium boron hydride to the ruthenium-based catalyst and, if required, heating the resulting mixture. Thereafter, the obtained reaction solution is subjected to solid-liquid separation by filtration, etc., to obtain solids. The thus obtained solids are fully washed with water and then dried at a temperature of preferably 60° C. or higher under normal pressure or under reduced pressure.

The reducing agent may be used in an amount of usually from about 1 to about 50 mol and preferably from 15 to 40 mol per one mol of the whole metal components supported on the ruthenium-based catalyst in order to effectively reduce the ruthenium component and the Group VIII metal component supported thereon.

Meanwhile, the above reducing treatment may be optionally carried out. After supporting the ruthenium component, etc., on the component (B) and/or the component (C) by hydrolysis with alkali, the solids obtained by solid-liquid separation of the resultant suspension may be fully washed with water and then dried. In the present invention, since the ruthenium component and the Group VIII metal component are supported on (B) the zirconia-containing composite oxide and/or (C) the zirconia surface-treated with a metal by the above hydrolysis method, it is not necessary to conduct a high-temperature calcination treatment usually required for an impregnation method, etc., and a high-temperature reducing treatment under an inert gas atmosphere, resulting in a simple procedure for production of the catalyst.

The thus produced ruthenium-based catalyst preferably contains the ruthenium component in an amount of from 0.01 to 25% by mass, more preferably from 0.1 to 20% by mass and still more preferably 1 to 15% by mass in terms of metallic ruthenium on the basis of a total amount of the catalyst including the carrier from the viewpoints of sufficient catalytic activity and selectivity and low costs. Also, from the same viewpoints as described above, the ruthenium-based catalyst preferably contains the Group VIII metal component in an amount of from 0.01 to 25% by mass, more preferably from 0.1 to 20% by mass and still more preferably 0.2 to 15% by mass in terms of Group VIII metal on the basis of a total amount of the catalyst including the carrier.

Further, in the ruthenium-based catalyst, the components (B) and (C) contain the metal oxide used together with zirconia, in an amount of preferably from 0.01 to 25% by mass and more preferably from 0.1 to 15% by mass in terms of the constitutional metal of the metal component on the basis of a total amount of the catalyst from the viewpoints of a good reactivity and a high selectivity to aliphatic primary amines.

The content of metallic ruthenium in the catalyst may be measured by subjecting the catalyst to fusion with ammonium hydrogensulfate and then subjecting the fused catalyst to ICP emission spectral analysis. The respective contents of the Group VIII metal component, the metal forming the composite oxide with zirconia and the metal with which zirconia is surface-treated may also be measured by ICP emission spectral analysis after subjecting the catalyst to wet decomposition treatment (using sulfuric acid/hydrogen peroxide) in the case where the zirconia contains no silicon, or to an alkali melting treatment in the case where the zirconia contains silicon.

In the process for producing an aliphatic amine according to the present invention, the aliphatic alcohol as the raw material is contacted with ammonia and hydrogen in the presence of the thus produced ruthenium-based catalyst to produce an aliphatic amine and preferably an aliphatic primary amine or an aliphatic secondary amine.

The contact reaction may be carried out in either a batch type closed system or a batch type flow system, or in a fixed bed flow system. The amount of the catalyst used varies depending upon the kind of reaction system used. In view of attaining good reactivity and selectivity, the catalyst is used in an amount of preferably from 0.1 to 20% by mass and more preferably from 0.1 to 10% by mass on the basis of the raw aliphatic alcohol.

Also, in view of good conversion and selectivity and prevention of deterioration of the catalyst, the reaction temperature is preferably from about 100 to about 280° C. and more preferably from 180 to 250° C., and the reaction pressure is usually from about normal pressures to about 40 MPaG and preferably from 0.5 to 30 MPaG for the batch type closed system, and usually from about normal pressures to about 10 MPaG and preferably from 0.1 to 5 MPaG for the batch type flow system.

The molar ratio of ammonia to the aliphatic alcohol as the raw materials (ammonia/aliphatic alcohol) is usually from about 0.1 to about 20 and preferably from 1 to 15 for the batch type closed system. In the batch type flow system or the fixed bed flow system, the molar ratio of ammonia flowed through the system to the aliphatic alcohol is preferably from 0.01 to 10 and more preferably from 0.1 to 8.

The molar ratio of hydrogen to the aliphatic alcohol as initial charges (hydrogen/aliphatic alcohol) is preferably from 0.01 to 3.0 and more preferably from 0.02 to 2.0 when used in a batch type closed system. When used in a batch type flow system or a fixed bed flow system, the molar ratio of hydrogen flowing through the system to the aliphatic alcohol is preferably from 0.01 to 1.0 and more preferably from 0.02 to 0.8. However, in any of the above reaction systems, the molar ratios in the course of the respective reactions are not particularly limited to the above-specified ranges.

EXAMPLES

The present invention is described in more detail by referring to the following Examples, etc. However, it should be noted that these Examples and Comparative Examples are only illustrative and not intended to limit the invention thereto.

Production Example 1

A separable flask was charged with 13.0 g of a zirconia powder and 220 g of ion-exchanged water to prepare a suspension, and then a solution prepared by dissolving 0.76 g of ruthenium chloride pentahydrate in 50 g of ion-exchanged water was added thereto, followed by heating the suspension to 60° C. while stirring. The thus obtained suspension (at 60° C.) was stirred for 3 h, and then aqueous ammonia as a precipitant was dropped therein to adjust a pH of the suspension to 11 for hydrolysis thereof, followed by aging the suspension for 2 h. Then, the suspension was mixed with 3.2 g of a 37% by mass formalin solution and heated to 90° C. at which the suspension was reduced for 1 h. Thereafter, the obtained powder was separated by filtration, washed with water and then dried at 60° C. under a pressure of 13 kPa, thereby obtaining about 13 g of a catalyst 1. The catalyst 1 was a catalyst formed by supporting 2% by mass of ruthenium on zirconia.

Production Example 2

The same procedure as in Production Example 1 was repeated except for using a zirconia/sulfuric acid powder in place of the zirconia powder, thereby obtaining about 13 g of a catalyst 2. The catalyst 2 was a catalyst formed by supporting 2% by mass of ruthenium on zirconia surface-treated with sulfur.

Production Example 3

A separable flask was charged with 13.0 g of a zirconia/sulfuric acid powder and 220 g of ion-exchanged water to prepare a suspension, and then a solution prepared by dissolving 0.38 g of ruthenium chloride pentahydrate and 0.93 g of nickel sulfate hexahydrate in 50 g of ion-exchanged water was added thereto, followed by heating the suspension to 60° C. while stirring. The thus obtained suspension (at 60° C.) was stirred for 3 h, and then aqueous ammonia as a precipitant was dropped therein to adjust a pH of the suspension to 11 for hydrolysis thereof, followed by aging the suspension for 2 h. Then, the suspension was mixed with 3.2 g of a 37% by mass formalin solution and heated to 90° C. at which the suspension was reduced for 1 h. Thereafter, the obtained powder was separated by filtration, washed with water and then dried at 60° C. under a pressure of 13 kPa, thereby obtaining about 13 g of a catalyst 3. The catalyst 3 was a catalyst formed by supporting 1% by mass of ruthenium and 1.6% by mass of nickel on zirconia surface-treated with sulfur.

Production Example 4

The same procedure as in Production Example 3 was repeated except for using a zirconia/cerium oxide powder in place of the zirconia/sulfuric acid powder, thereby obtaining about 13 g of a catalyst 4. The catalyst 4 was a catalyst formed by supporting 1% by mass of ruthenium and 1.6% by mass of nickel on a composite oxide of zirconium and cerium as the zirconia-containing composite oxide.

Production Example 5

The same procedure as in Production Example 3 was repeated except for using a zirconia/calcium oxide powder in place of the zirconia/sulfuric acid powder, thereby obtaining about 13 g of a catalyst 5. The catalyst 5 was a catalyst formed by supporting 1% by mass of ruthenium and 1.6% by mass of nickel on a composite oxide of zirconium and calcium as the zirconia-containing composite oxide.

Production Example 6

The same procedure as in Production Example 3 was repeated except for using a zirconia/lanthanum oxide powder in place of the zirconia/sulfuric acid powder, thereby obtaining about 13 g of a catalyst 6. The catalyst 6 was a catalyst formed by supporting 1% by mass of ruthenium and 1.6% by mass of nickel on a composite oxide of zirconium and lanthanum as the zirconia-containing composite oxide.

Production Example 7

The same procedure as in Production Example 3 was repeated except for using a zirconia/aluminum oxide powder in place of the zirconia/sulfuric acid powder, thereby obtaining about 13 g of a catalyst 7. The catalyst 7 was a catalyst formed by supporting 1% by mass of ruthenium and 1.6% by mass of nickel on a composite oxide of zirconium and aluminum as the zirconia-containing composite oxide.

Production Example 8

The same procedure as in Production Example 3 was repeated except for using a zirconia/yttrium oxide powder in place of the zirconia/sulfuric acid powder, thereby obtaining about 13 g of a catalyst 8. The catalyst 8 was a catalyst formed by supporting 1% by mass of ruthenium and 1.6% by mass of nickel on a composite oxide of zirconium and yttrium as the zirconia-containing composite oxide.

Production Example 9

The same procedure as in Production Example 3 was repeated except for using a zirconia/silica powder in place of the zirconia/sulfuric acid powder, thereby obtaining about 13 g of a catalyst 9. The catalyst 9 was a catalyst formed by supporting 1% by mass of ruthenium and 1.6% by mass of nickel on a composite oxide of zirconium and silicon as the zirconia-containing composite oxide.

Production Example 10

The same procedure as in Production Example 3 was repeated except for using a zirconia/titanium oxide powder in place of the zirconia/sulfuric acid powder, thereby obtaining about 13 g of a catalyst 10. The catalyst 10 was a catalyst formed by supporting 1% by mass of ruthenium and 1.6% by mass of nickel on a composite oxide of zirconium and titanium as the zirconia-containing composite oxide.

Production Example 11

The same procedure as in Production Example 3 was repeated except for supporting 2% by mass of ruthenium and 0.6% by mass of nickel on the zirconia-containing composite oxide, thereby obtaining about 13 g of a catalyst 11.

Properties of (B) the zirconia-containing composite oxides or (C) the zirconias surface-treated with a metal used in Production Examples 1 to 11 are shown in Table 1.

TABLE 1

| Production Examples | Contents of metal components other than zirconium (mol %) | Specific surface area (m$^2$/g) | Particle size (μm) | pH of dispersion |
|---|---|---|---|---|
| 1 | — | 90.4 | 1.3 | 7.9 |
| 2, 3, 11 | 4.4 | 165 | 3.7 | 4.1 |
| 4 | 4.9 | 113 | 3.8 | 4.9 |
| 5 | 3.9 | 86.6 | 2.0 | 8.3 |
| 6 | 9.7 | 170 | 4.1 | 6.6 |
| 7 | 8.7 | 201 | 4.1 | 5.2 |
| 8 | 9.5 | 130 | 3.8 | 4.5 |
| 9 | 5.7 | 138 | 3.7 | 5.1 |
| 10 | 4.9 | 103 | 3.9 | 5.4 |

Example 1

A 500 mL autoclave of an electromagnetic induction rotary agitation type was charged with 150 g (0.55 mol) of stearyl alcohol and 3 g of the catalyst 2 produced in Production Example 2 (2.0% by mass on the basis of the raw alcohol), and then 47 g (2.76 mol) of ammonia was charged into the autoclave and further 0.17 mol of hydrogen was introduced under pressure thereinto such that a whole pressure in the autoclave as measured at room temperature reached 2.3 MPa. Next, the contents of the autoclave were heated to a reaction temperature of 220° C. while stirring (at 1000 rpm). The initial maximum pressure in the autoclave at 220° C. was 16 MPa. While continuously supplying hydrogen into the autoclave such that a whole pressure therein was maintained at a constant pressure of 16 MPa, the contents of the autoclave were reacted with each other.

The resultant reaction product was filtered to remove the catalyst therefrom, and then subjected to gas chromatography to analyze a composition thereof. The reaction time required until reaching a reaction rate of 93% as well as the selectivity to each of stearyl amine and distearyl amine at the reaction ratio are shown in Table 2.

Comparative Example 1

The same procedure as in Example 1 was repeated except for the reaction was conducted using the catalyst 1 produced in Production Example 1 in place of the catalyst 2 produced in Production Example 2. The resulting product was evaluated in the same manner as in Example 1. The results are shown in Table 2.

TABLE 2

| | Catalyst | Reaction time (h) | Stearyl amine (%) | Distearyl amine (%) |
|---|---|---|---|---|
| Example 1 | 2 | 2.8 | 84.8 | 7.4 |
| Comparative Example 1 | 1 | 6.5 | 75.0 | 15.3 |

Examples 2 to 9

A 500 mL autoclave of an electromagnetic induction rotary agitation type was charged with 150 g (0.55 mol) of stearyl alcohol and 3 g of the respective catalysts 3 to 10 produced in Production Examples 3 to 10 (2.0% by mass on the basis of the raw alcohol), and then 47 g (2.76 mol) of ammonia was charged into the autoclave and further 0.17 mol of hydrogen was introduced under pressure thereinto such that a whole pressure in the autoclave as measured at room temperature reached 2.3 MPa. Next, the contents of the autoclave were heated to a reaction temperature of 220° C. while stirring (at 1000 rpm). The initial maximum pressure in the autoclave at 220° C. was 16 MPa. While continuously supplying hydrogen into the autoclave such that a whole pressure therein was maintained at a constant pressure of 16 MPa, the contents of the autoclave were reacted with each other.

The resultant reaction product was filtered to remove the catalyst therefrom, and then subjected to gas chromatography to analyze a composition thereof. The reaction time required until reaching a reaction ratio of 93% as well as the selectivity to each of stearyl amine and distearyl amine at the reaction rate are shown in Table 3.

Meanwhile, it was confirmed that the catalyst using the zirconia surface-treated with sulfur (catalyst 3) was more excellent from the viewpoint of reaction time.

TABLE 3

| Examples | Catalyst | Reaction time (h) | Stearyl amine (%) | Distearyl amine (%) |
|---|---|---|---|---|
| 2 | 3 | 2.4 | 91.8 | 7.1 |
| 3 | 4 | 3.3 | 90.9 | 8.2 |
| 4 | 5 | 8.0 | 92.5 | 6.9 |
| 5 | 6 | 6.1 | 91.4 | 7.7 |
| 6 | 7 | 5.8 | 91.1 | 8.2 |
| 7 | 8 | 6.1 | 92.6 | 6.5 |
| 8 | 9 | 4.8 | 92.4 | 7.0 |
| 9 | 10 | 4.2 | 92.0 | 7.2 |

Example 10

A 500 mL autoclave of an electromagnetic induction rotary agitation type was charged with 150 g (0.55 mol) of stearyl alcohol and 3 g of the catalyst 11 produced in Production Example 11 (2.0% by mass on the basis of the raw alcohol), and then a mixed gas of ammonia and hydrogen having partial pressures of 1.0 MPa and 1.0 MPa, respectively, was charged under pressure into the autoclave while controlling a flow rate of the mixed gas at an outlet to from 17 to 20 in terms of KG-2. Next, the contents of the autoclave were heated to a reaction temperature of 220° C. while stirring (at 1000 rpm). The reaction pressure at 220° C. was kept constant at 2.0 MPa. The resultant reaction product was filtered to remove the catalyst therefrom, and then subjected to gas chromatography to analyze a composition thereof. As a result, it was confirmed that when the reaction was conducted for 6.5 h, the conversion ratio of the raw alcohol was 100%, and the selectivity to distearyl amine was 48.73% by weight whereas the selectivity to stearyl amine was 13% by weight. Thus, it was possible to selectively produce the aliphatic secondary amine. Meanwhile, it was confirmed that when increasing the partial pressure of hydrogen relative to that of ammonia in the mixed gas charged, the selectivity to the secondary amine was able to be increased.

INDUSTRIAL APPLICABILITY

In the process for producing an aliphatic amine according to the present invention, an aliphatic primary amine and an aliphatic secondary amine can be produced from an aliphatic alcohol with a high catalytic activity and a high selectivity. The resultant aliphatic amines are important compounds in domestic and industrial application fields and are suitably used, for example, as raw materials for production of surfactants, fiber-treating agents, etc.

The invention claimed is:

1. A process for producing an aliphatic amine, comprising: contacting a linear, branched, or cyclic aliphatic alcohol having 6 to 22 carbon atoms with ammonia and hydrogen in the presence of a catalyst formed by supporting a ruthenium component on at least one material selected from the group consisting of (B) a zirconia-containing composite oxide and (C) zirconia surface-treated with a metal by hydrolysis of (A) a ruthenium compound.

2. The process according to claim 1, wherein the catalyst is formed by hydrolyzing (A) the ruthenium compound and (D) at least one metal compound selected from the group consisting of Group VIII metal compounds to support the ruthenium component and a Group VIII metal component on the at least one material selected from the group consisting of (B) the zirconia-containing composite oxide and (C) the zirconia surface-treated with a metal.

3. The process according to claim 2, wherein a content of the Group VIII metal component in the catalyst is from 0.01 to 25% by mass in terms of the Group VIII metal element on the basis of a total amount of the catalyst.

4. The process according to claim 1, wherein a content of the ruthenium component in the catalyst is from 0.01 to 25% by mass in terms of metallic ruthenium on the basis of a total amount of the catalyst.

5. The process according to claim 1, wherein (B) the zirconia-containing composite oxide is in the form of a composite oxide containing a zirconia component and at least one metal component selected from the group consisting of molybdenum, calcium, cerium, lanthanum, aluminum, yttrium, silicon, titanium, sulfur and phosphorus.

6. The process according to claim 1, wherein (C) the zirconia surface-treated with a metal is zirconia surface-treated with at least one metal component selected from the group consisting of molybdenum, calcium, cerium, lanthanum, aluminum, yttrium, silicon, titanium, sulfur and phosphorus.

7. The process according to claim 1, wherein (C) the zirconia surface-treated with a metal is obtained by impregnating zirconia with the at least one metal component selected from the group consisting of molybdenum, calcium, cerium, lanthanum, aluminum, yttrium, silicon, titanium, sulfur and phosphorus, or dispersing zirconia in a solution of a salt of the metal component, to support the metal component on zirconia, and then calcining the resulting metal component-supporting zirconia.

8. The process according to claim 1, wherein the catalyst is subjected to drying treatment at a temperature of 60° C. or higher.

9. The process according to claim 1, wherein the catalyst produced is subjected to reduction treatment in the presence of at least one reducing agent selected from the group consisting of formaldehyde, hydrazine and sodium boron hydride.

10. The process according to claim 1, wherein the contact reaction of the aliphatic alcohol with ammonia and hydrogen is carried out at a temperature of from 100 to 280° C.

11. The process according to claim 1, wherein the contact reaction of the aliphatic alcohol with ammonia and hydrogen is carried out under such a condition that a molar ratio of ammonia to the aliphatic alcohol (ammonia/aliphatic alcohol) is from 0.1 to 20.

12. The process according to claim 2, wherein a content of the Group VIII metal component in the catalyst is from 0.1 to 20% by mass in terms of the Group VIII metal element on the basis of a total amount of the catalyst.

13. The process according to claim 2, wherein a content of the Group VIII metal component in the catalyst is from 0.2 to 15% by mass in terms of the Group VIII metal element on the basis of a total amount of the catalyst.

14. The process according to claim 1, wherein a content of the ruthenium component in the catalyst is from 0.1 to 20% by mass in terms of metallic ruthenium on the basis of a total amount of the catalyst.

15. The process according to claim 1, wherein a content of the ruthenium component in the catalyst is from 1 to 15% by mass in terms of metallic ruthenium on the basis of a total amount of the catalyst.

16. The process according to claim 1, wherein the contact reaction of the aliphatic alcohol with ammonia and hydrogen is carried out at a temperature of from 180 to 250° C.

17. The process according to claim 1, wherein the contact reaction of the aliphatic alcohol with ammonia and hydrogen is carried out at a pressure of from atmospheric pressure to 40 MPaG.

18. The process according to claim 1, wherein the contact reaction of the aliphatic alcohol with ammonia and hydrogen is carried out at a pressure of from 0.5 MPaG to 30 MPaG.

19. The process according to claim 1, wherein the contact reaction of the aliphatic alcohol with ammonia and hydrogen is carried out under such a condition that a molar ratio of ammonia to the aliphatic alcohol (ammonia/aliphatic alcohol) is from 1 to 15.

* * * * *